(12) United States Patent
John et al.

(10) Patent No.: US 8,007,840 B2
(45) Date of Patent: *Aug. 30, 2011

(54) CONJUGATED DIENAMIDES, METHODS OF PRODUCTION THEREOF, COMPOSITIONS CONTAINING SAME AND USES THEREOF

(75) Inventors: Thumplasseril V. John, Morganville, NJ (US); Markus A. Eckert, Ramsey, NJ (US); Mark L. Dewis, Matawan, NJ (US); Jan Herman Colstee, MN Waalwijk (NL); Neil C. da Costa, Middletown, NJ (US)

(73) Assignee: International Flavors & Fragrances Inc., New York, NY (US)

(*) Notice: Subject to any disclaimer, the term of this patent is extended or adjusted under 35 U.S.C. 154(b) by 571 days.

This patent is subject to a terminal disclaimer.

(21) Appl. No.: 11/857,587

(22) Filed: Sep. 19, 2007

(65) Prior Publication Data
US 2008/0008810 A1    Jan. 10, 2008

Related U.S. Application Data

(62) Division of application No. 10/678,558, filed on Oct. 3, 2003.

(51) Int. Cl.
*A61K 36/67* (2006.01)
*A23L 2/56* (2006.01)

(52) U.S. Cl. .................... 424/734; 426/534
(58) Field of Classification Search .................. None
See application file for complete search history.

(56) References Cited

U.S. PATENT DOCUMENTS

| | | | | |
|---|---|---|---|---|
| 3,602,129 | A | * | 8/1971 | Cherre .............................. 99/282 |
| 6,054,585 | A | * | 4/2000 | Majeed et al. ................... 546/197 |
| 6,365,601 | B1 | * | 4/2002 | Gaikar et al. ................... 514/315 |

OTHER PUBLICATIONS

Yang et al., A Piperine Amide Extracted from Piper longum L. Fruit Shows Activity against Aedes aegypti Mosquito Larvae, 2002, J Agric Food Chem, 50: 3765-3767.*
Gokhale et al., Chemical investigation of the fruits of Piper longum, 1948, J University of Bombaby, Science: Physical Sciences, Mathematics, Biological Sciences and Medicine, 16 A: 47-52.*
Nigam et al., Ethereal oil from Piper longum berries, 1965, Riechstoffe, Aromen, Koerperflegemittel, 15: 451-2, 454, 456.*

* cited by examiner

*Primary Examiner* — Christopher R. Tate
*Assistant Examiner* — Catheryne Chen
(74) *Attorney, Agent, or Firm* — Elizabeth M. Quirk; XuFan Tseng; Joseph F. Leightner

(57) ABSTRACT

Described are mixtures of at least four of the alkadienamides defined according to the structure:

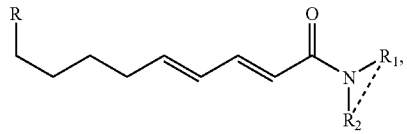

wherein R represents $C_1$-$C_2$ n-alkyl; $R_1$ is 2-methyl-1-propyl and $R_2$ is hydrogen, or $R_1$ and $R_2$ taken together is a moiety having the formula —$(CH_2)_n$—, wherein n is 4 or 5, or compositions containing substantial concentrations of such mixtures, prepared according to novel processes: (a) extraction of a ground substantially dried fruit of one of the *Piper* species, *Piper longum* Linn or *Piper peepuloides*; (b) natural product-forming synthesis; or (c) synthetic product-forming synthesis. Also described are uses of the thus-formed products for augmenting, enhancing or imparting an aroma, taste, chemesthetic effect and/or antibacterial effect in or to a consumable material and/or in the oral cavity and/or on the mammalian epidermis.

12 Claims, 5 Drawing Sheets

US 8,007,840 B2

CONJUGATED DIENAMIDES, METHODS OF PRODUCTION THEREOF, COMPOSITIONS CONTAINING SAME AND USES THEREOF

STATUS OF RELATED APPLICATIONS

This application is a divisional of U.S. Ser. No. 10/678,558, filed on Oct. 3, 2003, the contents hereby incorporated by reference as if set forth in its entirety.

FIELD OF THE INVENTION $C_{10}$-$C_{11}$-E2,E4-alkadienamide mixtures, obtainable synthetically or from a dried, ground *Piper* species, *Piper longum* Linn or *Piper peepuloides*, having beneficial flavor and sensory attributes in the oral cavity and on skin.

BACKGROUND OF THE INVENTION

The presence of $C_{10}$ and $C_{12}$ diene and triene amide derivatives in a wide variety of botanicals is known and the use thereof to impart flavor and/or a tingling and/or warming sensations in the oral cavity and on skin when used in foodstuffs, chewing gum, oral care products, hair care products, colognes, topical cosmetic products or medicinal products. Such $C_{10}$ and $C_{12}$ diene and triene amide derivatives are also disclosed as exhibiting biological activity, most notably antibacterial, anti-fungal and insecticidal activity. The most significant compounds which are members of the genus: "$C_{10}$ and $C_{12}$ diene and triene amide derivatives" are those disclosed as follows:

Spilanthol or affinin having the structure:

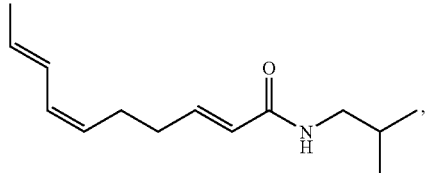

the use of which in oral care, skin care and medicinal products is disclosed in Nakanatsu et al, Published European Patent Application EP 1,121,927 A2.

Pellitorine (N-isobutyl-2,4-decadienamide) has the structure:

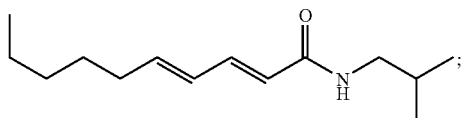

Iyeremide A (N-pyrrolidyl-2,4-decadienamide) has the structure:

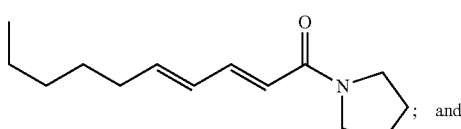
and

Iyeremide B (N-piperidyl-2,4-decadienamide) has the structure:

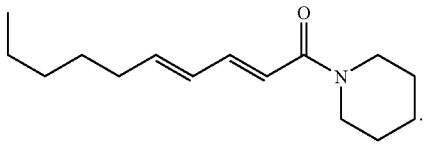

Piperine (N-piperidyl-5(3,4-methylenedioxyphenyl)-2,4-pentadienamide) and N-isobutyl-2,4-dodecadienamide are disclosed as constituents of *Piper guineense* stem by Adesina et al. in "GC/MS Investigations of the minor constituents of *Piper guineense* stem", Pharmazie 57 (2002)9, pages 622-627. It is indicated in the introduction of the Adesina paper: "*Piper guineense* Schum and Thonn, Piperaceae . . . leaves and fruits . . . have been used as condiments, flavorants and generally as spices in foods. The sharp peppery taste of the fruit has contributed to its acceptability and use in some food and drug preparations."

Piperine, N-piperidyl-5(3,4-methylenedioxyphenyl)-2,4-pentadienamide, is also disclosed in U.S. Pat. No. 6,365,601 as being extractable from the fruits of *Piper* species, including *Piper longum*, where it is present in a concentration of 4.5%. The corresponding 2,4-heptadienamide is also indicated to be extractable from *Piper longum* fruit by Das et al., "One New and Two Rare Alkamides from Two Samples of the Fruits of *Piper longum*", Natural Product Sciences, 4(1):23-25(1998).

However, nothing set forth in the prior art discloses mixtures of four or more $C_{10}$-$C_{11}$-E2,E4-alkadienamide, particularly in high concentration, e.g., between 3% and 100%, which mixtures are useful for their beneficial flavor and sensory attributes in the oral cavity and on skin. Furthermore, nothing in the prior art discloses such $C_{10}$-$C_{11}$-E2,E4-alkadienamide mixtures as extractable from the ground, dried fruit of the *Piper* species, *Piper longum* Linn or *Piper peepuloides*.

SUMMARY OF THE INVENTION

The invention is directed to mixtures of at least four $C_{10}$-$C_{11}$-E2,E4-alkadienamides, each of which alkadienamide is defined according to the structure:

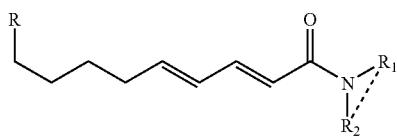

wherein R represents $C_1$-$C_2$ n-alkyl; $R_1$ is 2-methyl-1-propyl and $R_2$ is hydrogen, or $R_1$ and $R_2$ taken together is a moiety having the formula —$(CH_2)_n$—, wherein n is 4 or 5.

The mixtures of the invention are useful for augmenting, enhancing or imparting an aroma, taste, chemesthetic effect and/or antibacterial effect in or to a consumable material and/or the oral cavity and/or the human epidermis. The term, 'chemesthetic effect' is herein intended to mean the sensations, tingling, warming and salivation in the oral cavity, including lips and tingling and warming on the human epidermis. Thus, the mixtures of the invention are useful in such materials as perfume compositions, perfumed articles, including cosmetics, soaps, detergents and fine fragrance compositions, foodstuffs, chewing gums, non-alcoholic beverages, alcoholic beverages, oral care products such as mouth washes, toothpastes, cough drops, cough syrups and throat lozenges, and skin care products including skin creams and lotions and hair care products including anti-dandruff compositions and shampoos.

The mixtures of the invention are hereinafter referred to as "$C_{10}$-$C_{11}$-E2,E4-alkadienamide mixtures".

The $C_{10}$-$C_{11}$-E2,E4-alkadienamide mixtures of the invention may be obtained by means of (a) extraction of one of the *Piper* species, *Piper longum* Linn or *Piper peepuloides*, (b) natural product-forming synthesis or (c) synthetic-product forming synthesis. The invention is thus also directed to such $C_{10}$-$C_{11}$-E2,E4-alkadienamide mixture-forming processes.

Furthermore, the invention is directed to a process for augmenting, enhancing or imparting an aroma, taste, chemesthetic effect and/or antibacterial effect in or to a consumable material and/or the oral cavity and/or the human epidermis comprising the step of admixing with said consumable material and/or introducing into the oral cavity and/or applying to said human epidermis an aroma, taste, chemesthetic effect and/or antibacterial effect-effecting concentration and quantity of one or more of such $C_{10}$-$C_{11}$-E2,E4-alkadienamide mixtures.

DETAILED DESCRIPTION OF THE INVENTION

Figure 1:
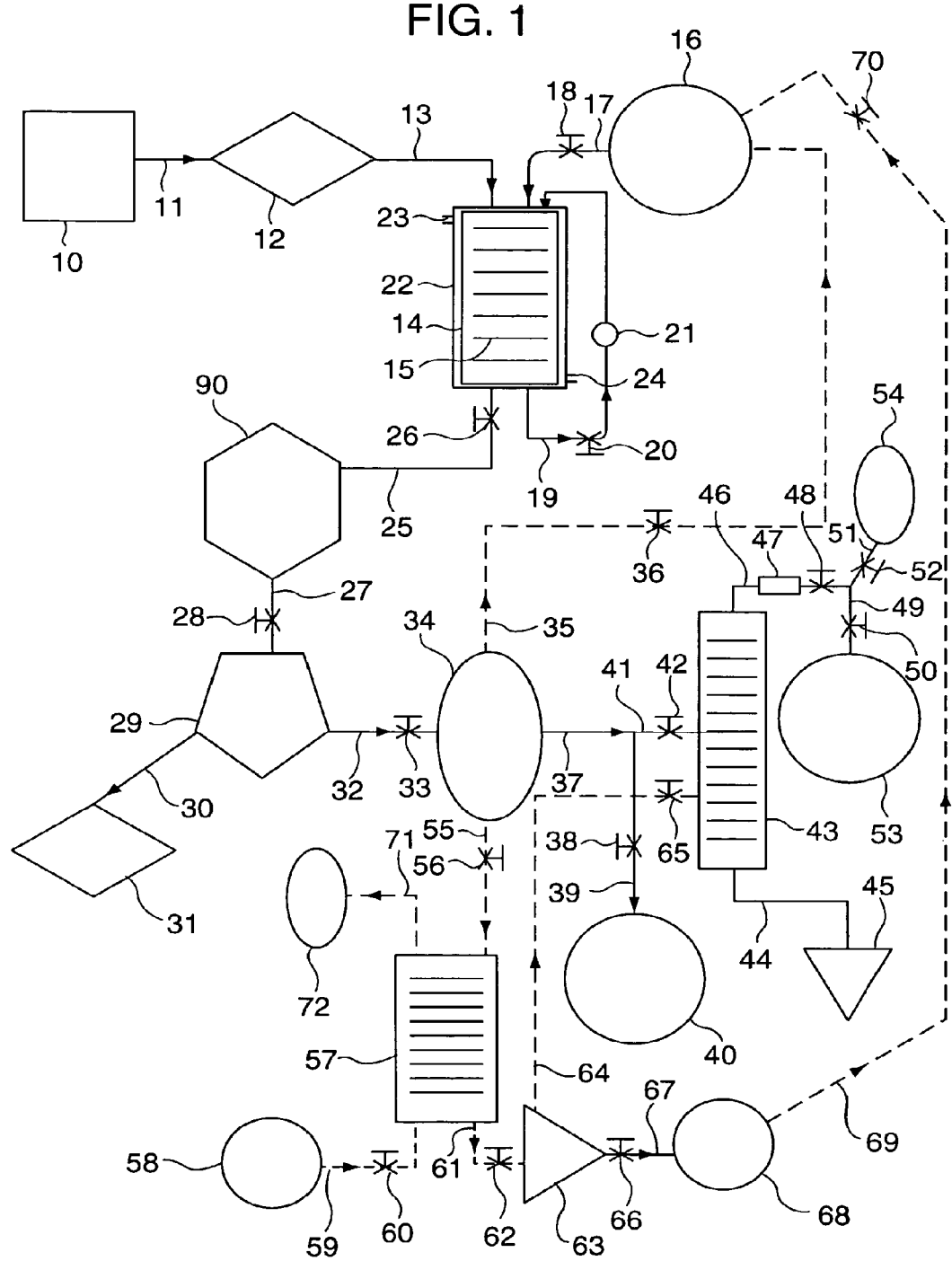
FIG. 1 is a schematic block flow diagram setting forth the process whereby the $C_{10}$-$C_{11}$-E2,E4-alkadienamide mixtures of the invention are obtained by means of extraction of one of the *Piper* species, *Piper longum* Linn or *Piper peepuloides*.

The $C_{10}$-$C_{11}$-E2,E4-alkadienamide mixtures of the invention preferably are utilized in the practice of the invention in concentrations of from about 3% to about 100% by weight of the product in which the mixtures are employed. In addition, the $C_{10}$-$C_{11}$-E2,E4-alkadienamide mixtures of the invention preferably include the components:

i. N-isobutyl-E2,E4-decadienamide;

ii. N-isobutyl-E2,E4-undecadienamide;

iii. N-pyrollidyl-E2,E4-decadienamide; and iv. N-piperidyl-E2,E4-decadienamide having the structures:

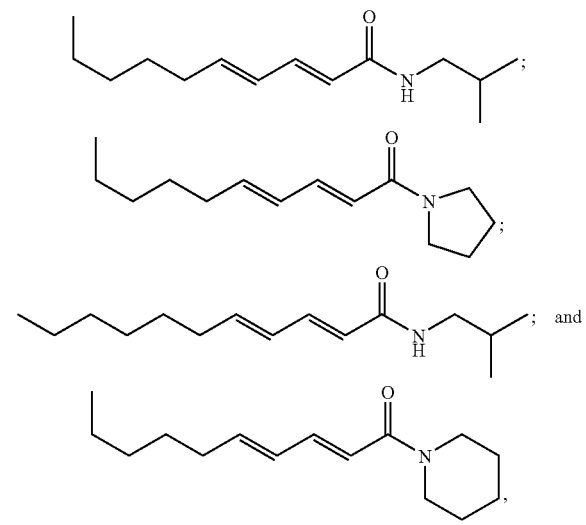

respectively.

When the $C_{10}$-$C_{11}$-E2,E4-alkadienamide mixtures of the invention are obtained by means of extraction of one of the *Piper* species, *Piper longum* Linn or *Piper peepuloides*, the process employed comprises the steps of:

i. milling dried fruits of at least one *Piper* species member selected from the group consisting of *Piper longum* Linn and *Piper peepuloides* in order to form a *Piper longum* Linn or *Piper peepuloides* powder having an average particle size in the range of from about 300 microns to about 800 microns;

ii. providing an extractor equipped with porous extractor plates, preferably a percolator having screen-equipped baskets;

iii. placing portions of the milled *Piper longum* Linn or *Piper peepuloides* powder on each of said porous extractor plates;

iv. intimately contacting the thus-supported milled *Piper longum* Linn or *Piper peepuloides* powder with a first quantity of a circulating given polar or non-polar solvent such as n-hexane at a temperature in the range of from about 30° C. to about 50° C. for a period of time of from about 10 hours to about 20 hours with the solvent to solids weight ratio being from about 2.75:1 to about 3.25:1 thereby forming a first extract and initially-extracted milled *Piper longum* Linn powder;

v. removing said first extract from the extractor;

vi. contacting the initially-extracted milled *Piper longum* Linn or *Piper peepuloides* powder with a second quantity of a circulating given polar or non-polar solvent, e.g., n-hexane at a temperature in the range of from about 30° C. to about 50° C. for a period of time of from about 10 hours to about 20 hours with the solvent to solids weight ratio being from about 1.75:1 to about 2.25:1 thereby forming a second extract and doubly-extracted milled *Piper longum* Linn or *Piper peepuloides* powder;

vii. removing said second extract from the extractor;

viii. contacting the doubly-extracted milled *Piper longum* Linn or *Piper peepuloides* powder with a third quantity of a circulating given polar or non-polar solvent, e.g., n-hexane at a temperature in the range of from about 30° C. to about 50° C. for a period of time of from about 10 hours to about 20 hours with the solvent to solids weight ratio being from about 0.75:1 to about 1.25:1 thereby forming a third extract and triply-extracted milled *Piper longum* Linn or *Piper peepuloides* powder;

ix. removing said third extract from the extractor;

x. combining said first extract, said second extract and said third extract thereby forming a combined extract;

xi. subjecting the resulting combined extract to the unit operation of evaporation thereby forming a concentrated extract; and xii. optionally fractionally distilling the resulting concentrated extract at a vapor temperature in the range of from about 55° C. to about 76° C., a liquid temperature in the range of from about 109° C. to about 203° C. and a pressure of in the range of from about 30 mm Hg to about 60 mm Hg thereby forming a distillate.

Preferred variations of the above described process are as follows:

(a) the concentrated extract formed as a result of carrying out step xi is extracted with 95% aqueous ethanol and the resulting ethanol extract is subjected to the unit operation of evaporation thereby forming a concentrated extract;

(b) the circulating extraction solvent is 95% aqueous ethanol and the optional fractional distillation step, xii, is not carried out; and.

(c) the circulating extraction solvent is 95% aqueous ethanol and, immediately subsequent to carrying out the unit operation of evaporation, step xi, the concentrated extract is extracted with n-hexane thereby forming a fourth extract; the fourth n-hexane extract is subjected to the unit operation of evaporation thereby forming a concentrated extract and the thus-concentrated extract is fractionally distilled at a vapor temperature in the range of from about 55° C. to about 76° C., a liquid temperature in the range of from about 109° C. to about 203° C. and a pressure of in the range of from about 30 mm Hg to about 60 mm Hg thereby forming a distillate.

In addition, the above mentioned process may also comprise the additional step of admixing the resulting extract, when the distillation step is not employed, or distillate with a food-grade diluent.

When the $C_{10}$-$C_{11}$-E2,E4-alkadienamide mixture components of the invention are obtained by means of natural product-forming synthesis, the process employed comprises the steps of:

i. forming a natural amine selected from the group consisting of isobutyl amine, piperidine and pyrrolidine;

ii. forming a natural amine acid salt thereof;

iii. optionally neutralizing the resulting amine salt to form the corresponding amine;

iv. providing a natural E2,E4-dienal selected from the group consisting of E2,E4-decadienal and E2,E4-undecadienal;

v. air oxidizing or microbiologically oxidizing the resulting E2,E4-dienal thereby forming the corresponding E2,E4-dienoic acid;

vi. esterifying the resulting E2,E4-dienoic acid with natural alkanol or natural glycerol thereby forming the corresponding E2,E4-dienoic acid ester;

vii. reacting the resulting E2,E4-dienoic acid ester with the natural amine salt formed in step ii or the natural amine formed in step iii in the presence of an ester-forming enzyme, such as lipase; and viii. recovering the resulting amide.

The resulting individual amides are then admixed with one another thereby forming the mixture of $C_{10}$-$C_{11}$-E2,E4-alkadienamide components of the invention.

In the above described process, when the amine initially formed is isobutyl amine, it is preferably produced by reacting natural valine with a natural aromatic ketone or aromatic aldehyde to form an imine carboxylic acid; isomerizing and decarboxylating the resulting imine carboxylic acid to form a decarboxylated imine; hydrolyzing the resulting decarboxylated imine at a pH of from about 1.5 to about 3.5 thereby forming the natural isobutyl amine salt.

Preferably, the esterification in step vi. above of the E2,E4-dienoic acid is carried out with natural ethanol.

Thus, for example, in accordance with the above described generic process, the specific process for the production of natural N-isobutyl-E2,E4-decadienamide having the structure:

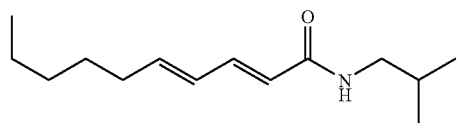

comprising the steps of:

i. forming natural isobutyl amine acid salt by (a) reacting natural valine with natural anisaldehyde to form an imine; (b) isomerizing the imine and effecting decarboxylation thereof thereby forming a decarboxylated imine; and (c) effecting acid hydrolysis of the decarboxylated imine thereby forming the acid salt of isobutyl amine; and (d) optionally neutralizing the acid salt of isobutyl amine to form isobutyl amine;

ii. forming natural ethyl 2E,4E-decadienoate by (a) thermal isomerization of natural ethyl 2Z,4E-decadienoate; (b) air oxidation of natural 2E,4E-decadienal in admixture with ethanol; or (c) microbiological oxidation of natural 2E,4E-decadienal;

iii. reacting the resulting ethyl 2E,4E-decadienoate with the natural isobutyl amine or salt thereof in the presence of an esterification enzyme with the mole ratio of decadienoate:amine or salt thereof being from 1:1 to about 3:1 at a temperature of from about 30° C. to about 80° C. for a period of time of from about 20 to about 100 hours according to the reaction:

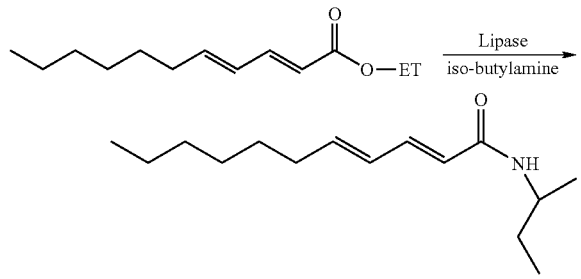

and iv. recovering the resulting natural N-isobutyl-E2,E4-decadienamide.

When the $C_{10}$-$C_{11}$-E2,E4-alkadienamide mixture components of the invention are obtained by means of synthetic product-forming synthesis, the process employed comprises the steps of dissolving an E2,E4-dienoic acid selected from the group consisting of E2,E4-decadienoic acid and E2,E4-undecadienoic acid in a compatible solvent thereby forming a E2,E4-dienoic acid solution; admixing the resulting E2,E4-dienoic acid solution with from about 1 to about 2 equivalents of an acid-activating reagent selected from the group consisting of a lower alkyl haloformate, an N,N'-dialiphatic or cycloaliphatic azodicarbodiimide and a dihalo-oxalate at a temperature in the range of from about 0° C. to about 20° C. thereby forming an intermediate; cooling the resulting intermediate-containing solution to a temperature in the range of from about −10° C. to about +10° C. and, when using as a reactant the lower alkyl haloformate or the dihalooxalate, admixing therewith a tri-loweralkyl amine while maintaining the temperature of the mixture below +10° C.; then aging the resulting intermediate-containing product at ambient conditions for a period of from about 0.5 to about 3 hours, according to the reaction:

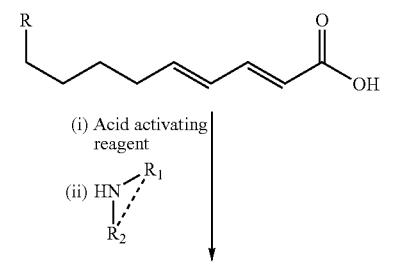

filtering the resulting product; separating the resulting filtrate and cooling the resulting filtrate to a temperature in the range of from about −5° C. to +5° C.; admixing the resulting cooled filtrate with from about 1 to about 4 equivalents of an amine selected from the group consisting of isobutyl amine, piperidine and pyrrolidine at ambient conditions thereby effecting an amidation reaction, and thereby forming an amide defined according to the structure:

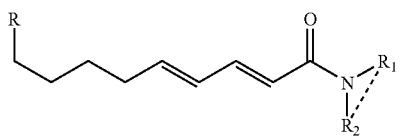

and recovering the resulting amide.

The resulting individual amides are then admixed with one another thereby forming the mixture of $C_{10}$-$C_{11}$-E2,E4-alkadienamide components of the invention.

When using as an acid activating agent ethyl chloroformate, the reaction proceeds as follows:

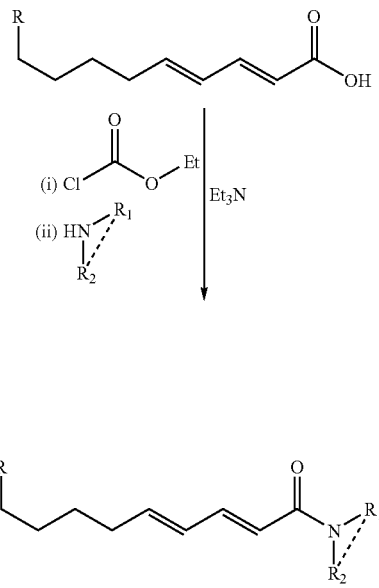

The thus-formed mixtures of $C_{10}$-$C_{11}$-E2,E4-alkadienamide components of the invention may each be admixed with a substantial quantity and concentration of a tingling sensate, for example, one or more of such sensates selected from the group consisting of substantially pure spilanthol having the structure:

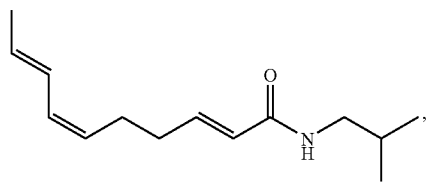

*Acmella ciliata, Acmella (Spilanthes) oppositifolia, Anacyclus pyrethrum* D.C., *Spiltanthes acmella* L. var. *oleraceae* (Jambu) and *Heliopsis longipes* S.F. Blake (*Chilcuan*) and the resulting mixtures may then be used for augmenting, enthancing or imparting an aroma, taste, chemesthetic effect and/or antibacterial effect in or to a consumable material and/or the oral cavity and/or the human epidermis by means of a process comprising the step of admixing with said consumable material and or introducing into the oral cavity and/or applying to said human epidermis an aroma, taste, chemesthetic effect and/or antibacterial effect-effecting concentration and quantity of the resulting mixture.

The following Table I sets forth examples of processes and compositions where the mixtures of $C_{10}$-$C_{11}$-E2,E4-alkadienamide components of the invention are utilized. Each of the useful ingredients set forth in the cited U.S. Patent and patent application references, including the examples thereof is usable in the practice of the invention, and hereby incorporated by reference.

TABLE I

| Nature of Use of the mixtures of $C_{10}$-$C_{11}$-E2,E4-alkadienamide components of the Invention | Reference Containing Examples Where the mixtures of $C_{10}$-$C_{11}$-E2,E4-alkadienamide components of the Invention are Utilizable |
|---|---|
| Skin care | U.S. Pat. No. 6,096,324 |
| Skin care moisturizers and cleaners | U.S. Pat. No. 6,099,849 |
| Cosmetic compositions | U.S. Pat. No. 6,190,679 |
| Oral sensates, flavor enhancers and potentiators | Application for U.S. Patent 2002/0122778 A1 published on Sep. 5, 2002 |
| Aroma compositions for foodstuffs and oral hygiene | Application for U.S. Patent 2003/0096731 A1 published on May 22, 2003 |
| Use of ferulic acid amides as flavor compounds | Application for U.S. Patent 2003/0152682 A1 published on Aug. 14, 2003 |
| Food, pharmaceutical and personal care products | European Published Application EP 1,121,927 A2 published Aug. 8, 2001 |
| Anti-dandruff and anti-itch compositions | Application for U.S. patent Ser. No. 10/067,596 filed on Feb. 5, 2002 |
| Taste and sensory effect compositions | Application for U.S. patent Ser. No. 10/411,672 filed on Apr. 11, 2003 |

As used herein olfactory effective amount is understood to mean the amount of compound in flavor compositions, oral care compositions, nasal care compositions, skin care compositions, hair and scalp care compositions, cosmetic compositions and other consumable materials as defined supra, the individual component will contribute to its particular olfactory characteristics, but the flavor, taste and aroma effect on the overall composition will be the sum of the effects of each of the flavor ingredients. As used herein taste effects include bitterness and tingling effects. Thus the compounds of the invention can be used to alter the taste characteristics of the flavor composition by modifying the taste reaction contributed by another ingredient in the composition. The amount will vary depending on many factors including other ingredients, their relative amounts and the effect that is desired.

The level of use of the mixtures of $C_{10}$-$C_{11}$-E2,E4-alkadienamide components of the invention in products is greater than 10 parts per billion, generally provided at a level of from about 50 parts per billion to about 200 parts per million in the finished product, more preferably from about 100 parts per billion to about 100 parts per million by weight.

The usage level of the mixtures of $C_{10}$-$C_{11}$-E2,E4-alkadienamide components of the invention varies depending on the product in which the mixtures of $C_{10}$-$C_{11}$-E2,E4-alkadienamide components of the invention are employed. For example, alcoholic beverages the usage level is from about 0.5 to about 25 parts per million, preferably from about 2 to about 10 and most preferably from about 5 to about 10 parts per million by weight. Non-alcoholic beverages are flavored at levels of from about 25 parts per billion to about 2 parts per million, preferably from about 100 parts per billion to about 0.5 parts per million and in highly preferred situations of from about 150 to about 400 parts per billion. Snack foods can be advantageously flavored using the mixtures of $C_{10}$-$C_{11}$-E2,E4-alkadienamide components of the invention at levels of from about 5 to about 250 parts per million, preferably from about 25 to about 200 and most preferably from about 35 to about 75 parts per million by weight.

The term "foodstuff" as used herein includes both solid and liquid ingestible materials for man or animals, which materials usually do, but need not, have nutritional value. Thus, foodstuffs include meats, gravies, soups, convenience foods, malt, alcoholic and other beverages, milk and dairy products, seafood, including fish, crustaceans, mollusks and the like, candies, vegetables, cereals, soft drinks, snacks, dog and cat foods, other veterinary products and the like.

When the mixtures of $C_{10}$-$C_{11}$-E2,E4-alkadienamide components of the invention are used in a flavoring composition, they can be combined with conventional flavoring materials or adjuvants. Such co-ingredients or flavor adjuvants are well known in the art for such use and have been extensively described in the literature. Requirements of such adjuvant materials are: (1) that they be non-reactive with the components of the mixtures of $C_{10}$-$C_{11}$-E2,E4-alkadienamides of the invention (2) that they be organoleptically compatible with the components of the mixtures of $C_{10}$-$C_{11}$-E2,E4-alkadienamides of the invention whereby the flavor of the ultimate consumable material to which the components of the mixtures of $C_{10}$-$C_{11}$-E2,E4-alkadienamides of the invention are added is not detrimentally affected by the use of the adjuvant; and (3) that they be ingestible acceptable and thus nontoxic or otherwise non-deleterious. Apart from these requirements, conventional materials can be used and broadly include other flavor materials, vehicles, stabilizers, thickeners, surface active agents, conditioners and flavor intensifiers.

Such conventional flavoring materials include saturated fatty acids, unsaturated fatty acids and amino acids; alcohols including primary and secondary alcohols, esters, carbonyl compounds including ketones, lactones; other cyclic organic materials including benzene derivatives, acyclic compounds, heterocyclics such as furans, pyridines, pyrazines and the like; sulfur-containing compounds including thiols, sulfides, disulfides and the like; proteins; lipids, carbohydrates; so-called flavor potentiators such as monosodium glutamate; magnesium glutamate, calcium glutamate, guanylates and inosinates; natural flavoring materials such as hydrolyzates, cocoa, vanilla and caramel; essential oils and extracts such as anise oil, clove oil and the like and artificial flavoring materials such as vanillyl butyl ether, ethyl vanillin and the like.

Specific preferred flavor adjuvants include but are not limited to the following: anise oil; ethyl-2-methyl butyrate; vanillin; cis-3-heptenol; cis-3-hexenol; trans-2-heptenal; butyl valerate; 2,3-diethyl pyrazine; methyl cyclo-pentenolone; benzaldehyde; valerian oil; 3,4-dimethoxyphenol; amyl acetate; amyl cinnamate; γ-butyryl lactone; furfural; trimethyl pyrazine; phenyl acetic acid; isovaleraldehyde; ethyl maltol; ethyl vanillin; ethyl valerate; ethyl butyrate; cocoa extract; coffee extract; peppermint oil; spearmint oil; clove oil; anethol; cardamom oil; wintergreen oil; cinnamic aldehyde; ethyl-2-methyl valerate; γ-hexenyl lactone; 2,4-decadienal; 2,4-heptadienal; methyl thiazole alcohol (4-methyl-5-β-hydroxyethyl thiazole); 2-methyl butanethiol; 4-mercapto-2-butanone; 3-mercapto-2-pentanone; 1-mercapto-2- propane; benzaldehyde; furfural; furfuryl alcohol; 2-mercapto propionic acid; alkyl pyrazine; methyl pyrazine; 2-ethyl-3-methyl pyrazine; tetramethyl pyrazine; polysulfides; dipropyl disulfide; methyl benzyl disulfide; alkyl thiophene; 2,3-dimethyl thiophene; 5-methyl furfural; acetyl furan; 2,4-decadienal; guaiacol; phenyl acetaldehyde; β-decalactone; d-limonene; acetoin; amyl acetate; maltol; ethyl butyrate; levulinic acid; piperonal; ethyl acetate; n-octanal; n-pentanal; n-hexanal; diacetyl; monosodium glutamate; monopotassium glutamate; sulfur-containing amino acids, e.g., cysteine; hydrolyzed vegetable protein; 2-methylfuran-3-thiol; 2-methyldihydrofuran-3-thiol; 2,5-dimethylfuran-3-thiol; hydrolyzed fish protein; tetramethyl pyrazine; propyl-propenyl disulfide; propylpropenyl trisulfide; diallyl disulfide; diallyl trisulfide; dipropenyl disulfide; dipropenyl trisulfide; 4-methyl-2-[(methylthio)-ethyl] -1,3-dithiolane; 4,5-dimethyl-2-(methylthiomethyl)-1,3-dithiolane; and 4-methyl-2-(methylthiomethyl)-1,3-dithiolane.

The components of the mixtures of $C_{10}$-$C_{11}$-E2,E4-alkadienamides of the invention or compositions incorporating them, as mentioned above, can be combined with one or more vehicles or carriers for adding them to the particular product. Vehicles can be water-soluble or oil-soluble edible or otherwise suitable materials such as triacetin, vegetable oil, triethyl citrate, ethyl alcohol, propylene glycol, water and the like. Carriers include materials such as gum arabic, carrageenan, xanthan gum, guar gum and the like.

Components of the mixtures of $C_{10}$-$C_{11}$-E2,E4-alkadienamides of the invention prepared according to the invention can be incorporated with the carriers by conventional means such as spray-drying, extrusion, drum-drying and the like. Such carriers can also include materials for coacervating the components of the mixtures of $C_{10}$-$C_{11}$-E2,E4-alkadienamides of the invention to provide encapsulated products, as set forth supra. When the carrier is an emulsion, the flavoring composition can also contain emulsifiers such as mono- and diglycerides or fatty acids and the like. With these carriers or vehicles, the desired physical form of the compositions can be prepared.

The quantity of the components of the mixtures of $C_{10}$-$C_{11}$-E2,E4-alkadienamides of the invention utilized should be sufficient to impart the desired flavor characteristic to the product, but on the other hand, the use of an excessive amount of the components of the mixtures of $C_{10}$-$C_{11}$-E2,E4-alkadienamides of the invention is not only wasteful and uneconomical, but in some instances, too large a quantity may unbalance the flavor or other organoleptic properties of the product consumed. The quantity used will vary depending upon the ultimate foodstuff, the amount and type of flavor initially present in the foodstuff; the further process or treatment steps to which the foodstuff will be subjected; regional and other preference factors; the type of storage, if any, to which the product will be subjected; and the preconsumption treatment such as baking, frying and so on, given to the product by the ultimate consumer. Accordingly, the terminology "effective amount" and "sufficient amount" is understood in the context of the present invention to be quantitatively adequate to alter the flavor of the foodstuff.

Referring to FIG. 1 dried *Piper longum* Linn or *Piper peepuloides* fruit at location 10 is transported via conveyor 11 into milling apparatus 12 wherein it is milled to a particle size in the range of from about 300 microns to about 800 microns. The milled particles are conveyed via line 13 into extractor 14 onto supported screens 15 (acting as extraction column stages). The temperature profiles and rates of heat transfer in extractor (percolator) 14 are controlled by means of fluid pumped into heating jacket 22 entering at inlet 24 and exiting at outlet 23. Extraction solvent (e.g., n-hexane) flows from solvent supply vessel 16 past control valve 18 through line 17 into extractor (percolator) 14, with the extraction solvent being recirculated through the supported screens and through line 19 past valve 20 using circulating solvent pump 21. After a period of time in the range of 10-20 hours, with the solvent: solids ratio being from about 2.75:1 to 3.25:1 the operation of the pump 21 is temporarily discontinued while the liquid extract containing extracted product is removed from the extractor via line 25 past control valve 26 into extract holding tank 90. Then, for a second time, extraction solvent, such as n-hexane, flows from solvent supply vessel 16 past control valve 18 through line 17 into extractor (percolator) 14, with the extraction solvent being recirculated through the supported screens and through line 19 past valve 20 using circulating solvent pump 21. After a period of time in the range of 10-20 hours, with the solvent:solids ratio being from about 1.75:1 to 2.25:1 the operation of the pump 21 is temporarily discontinued while the liquid extract containing extracted product is removed from the extractor via line 25 past control valve 26 into extract holding tank 90. Then, for a third time, extraction solvent, such as n-hexane, flows from solvent supply vessel 16 past control valve 18 through line 17 into extractor, also known as percolator, 14, with the extraction solvent being recirculated through the supported screens and through line 19 past valve 20 using circulating solvent pump 21. After a period of time in the range of 10-20 hours, with the solvent: solids ratio being from about 0.75:1 to 1.25:1 the operation of the pump 21 is discontinued while the liquid extract containing extracted product is removed from the extractor via line 25 past control valve 26 into extract holding tank 90. The combined extracts in holding vessel 90 is then passed through line 27 past control valve 28 into filtration apparatus 29 where precipitate is discarded via conveyor 30 to disposal means 31 and filtrate passes through line 32 past control valve 33 into evaporator 34. On operation of evaporator 34, overhead solvent vapor is recycled via line 35 past control valve 36 back to solvent supply vessel 16. Concentrated extract is passed through line 37 past control valve 38 into storage vessel 40. In the alternative, concentrated extract is passed through line 41 past control valve 42 into fractional distillation column 43 where residue is removed through line 44 and passed into disposal means 45 and overhead distillate (containing $C_{10}$-$C_{11}$-E2,E4-alkadienamide mixtures of the invention) is passed through line 46 and heat exchanger 47 past control valve 48 into product vessel 53 through line 49 past control valve 50; and into 'discarded fraction' vessel 54 through line 51 past control valve 52. In the alternative, when the circulating extraction solvent through extractor 14 is ethanol, concentrated extract is passed through line 55 past control valve 56 into liquid-liquid multistage extraction column 57 (equipped for n-hexane:ethanol exchange) while simultaneously passing n-hexane from storage vessel 58 through line 59 past control valve 60 into multi-stage extractor 57 countercurrent to the flow of the concentrated extract entering the multistage extractor 57 from line 34. Ethanol fraction exits from extractor 57 via line 71 into ethanol fraction storage vessel 72. n-Hexane extract exiting the extractor 57 through line 61 past control valve 62 is concentrated in evaporator 63. Hexane solvent exiting evaporator 63 passes through line 67 past valve 66 into vessel 68 from which the solvent is recycled via line 69 past control valve 70 into an alternative solvent supply vessel (which is separate from a solvent supply vessel that would be the source of ethanol supply) 16. Simultaneously, concentrated hexane extract exits from evaporator 63 via line 64 past control valve 65 into distillation column 43 where residue is removed through line 44 and passed into disposal means 45 and overhead distillate, containing $C_{10}$-$C_{11}$-E2,E4-alkadienamide mixtures of the invention, is passed through line 46 and heat exchanger 47 past control valve 48 into product vessel 53 through line 49 past control valve 50; and into discarded fraction vessel 54 through line 51 past control valve 52.

Figure 2:
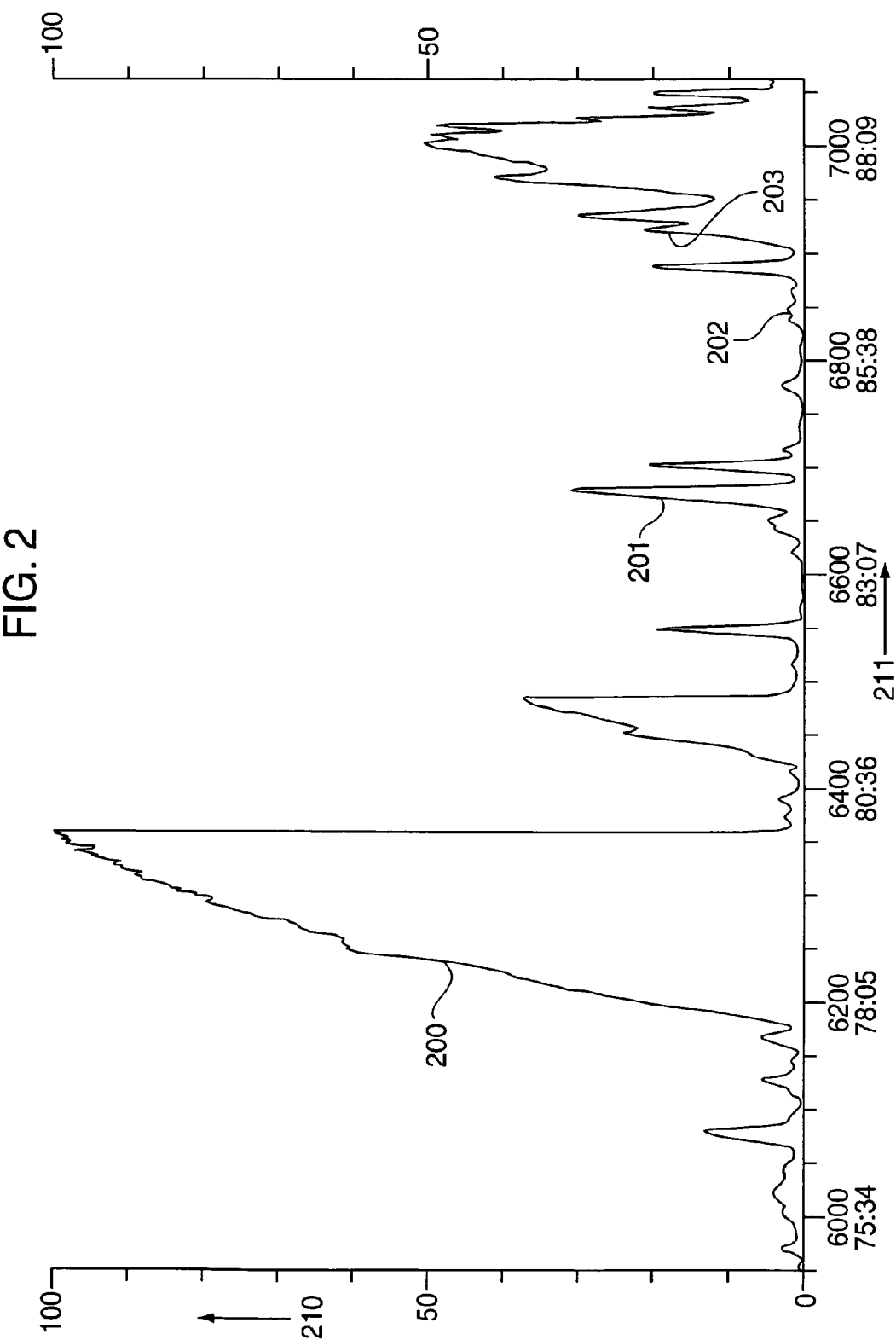
FIG. 2 is a portion of the GC-mass spectrum of the extract prepared according to the process whereby $C_{10}$-$C_{11}$-E2,E4-alkadienamide mixtures of the invention are obtained by means of extraction of the *Piper* species, *Piper longum* Linn.

Referring to FIG. 2, the "X" axis, horizontal axis, is indicated by reference numeral 211 and the "Y" axis is indicated by reference numeral 210. The peak indicated by reference numeral 200 is for N-isobutyl-E2,E4-decadienamide. The peak indicated by reference numeral 201 is for N-isobutyl-E2,E4-undecadienamide. The peak indicated by reference numeral 202 is for N-pyrrolidyl-E2,E4-decadienamide. The peak indicated by reference numeral 203 is for N-piperidyl-E2,E4-decadienamide.

Figure 3:
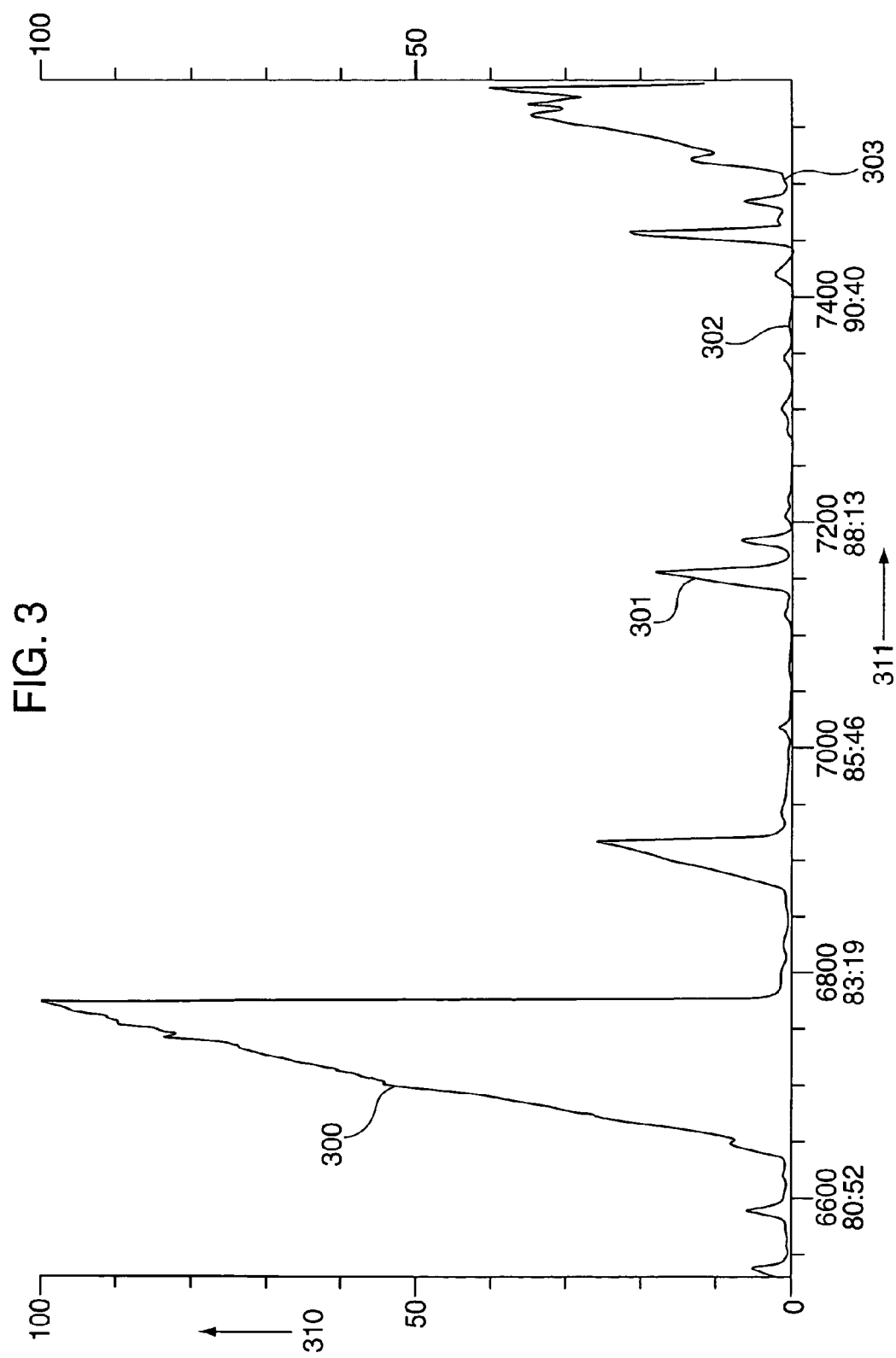
FIG. 3 is a portion of the GC-mass spectrum of the extract prepared according to the process whereby $C_{10}$-$C_{11}$-E2,E4-alkadienamide mixtures of the invention are obtained by means of extraction of the *Piper* species, *Piper peepuloides*.

Referring to FIG. 3, the "X" axis, horizontal axis, is indicated by reference numeral 311 and the "Y" axis is indicated by reference numeral 310. The peak indicated by reference numeral 300 is for N-isobutyl-E2,E4-decadienamide. The peak indicated by reference numeral 301 is for N-isobutyl-E2,E4-undecadienamide. The peak indicated by reference numeral 302 is for N-pyrrolidyl-E2,E4-decadienamide. The peak indicated by reference numeral 303 is for N-piperidyl-E2,E4-decadienamide.

Figure 4:
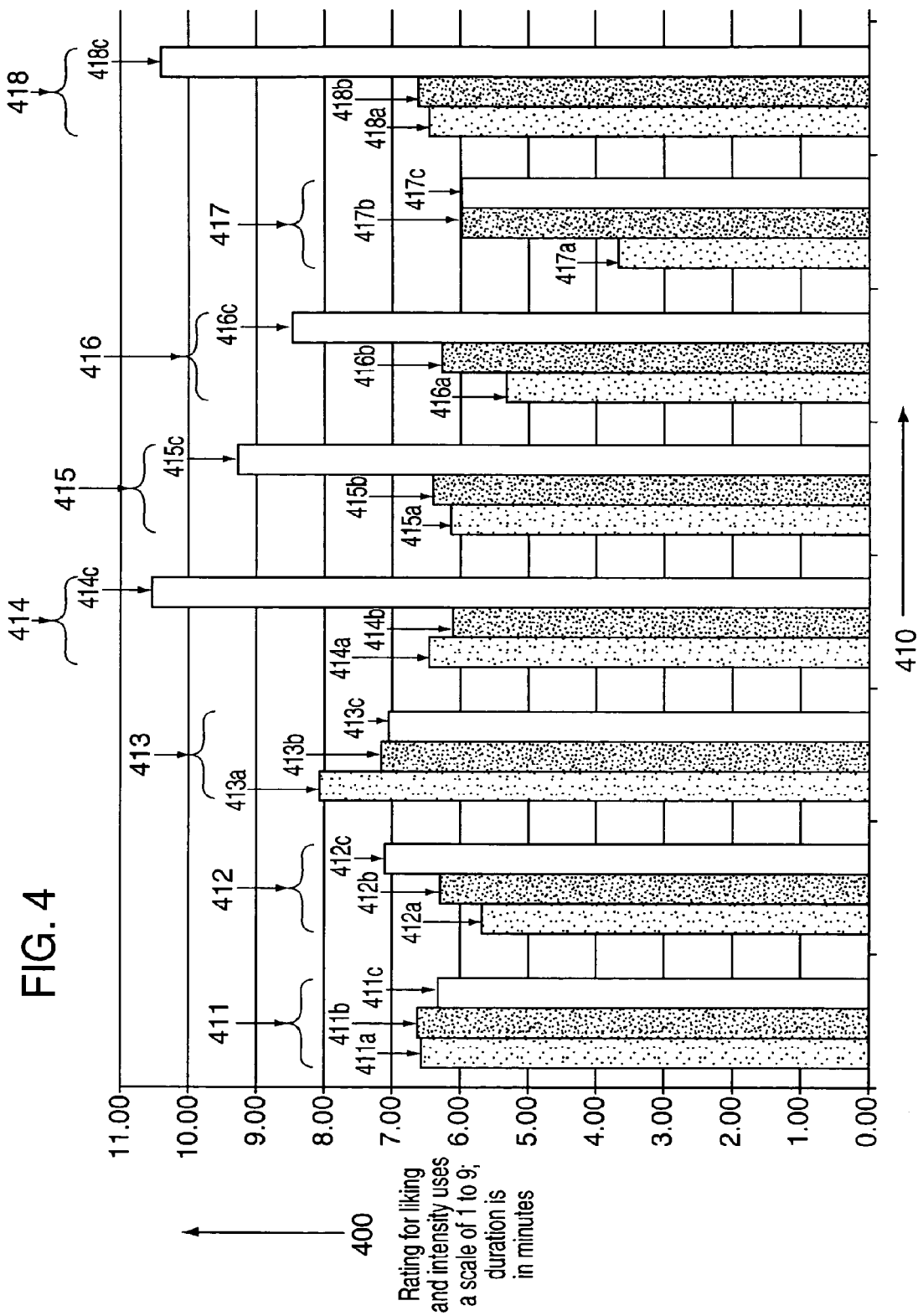
FIG. 4 is a set of comparative bar graphs setting forth (a) rating for liking on a scale of 1-9; (b) rating for intensity on a scale of 1-9 and (c) duration in minutes for (i) extracts of *Piper longum* Linn and *Piper peepulides* containing various concentrations of $C_{10}$-$C_{11}$-E2,E4-alkadienamide mixtures of the invention, (ii) pellitorine, and (iii) other sensate substances.

Referring to FIG. 4, the "Y" axis, indicated by reference numeral 400 indicates (a) the scale of 1-9 for measuring liking and intensity and (b) duration in minutes. The "X" axis, the horizontal axis, is indicated by reference numeral 410. The bar graphs indicated with the suffix "a" are for intensity. The bar graphs indicated by the suffix "b" are for liking. The bar graphs indicated by the suffix "c" are for duration.

The following Table II sets forth the specific substance being compared identified by a specific reference numeral:

TABLE II

| Substance being compared | Reference Numeral |
| --- | --- |
| Jambu Extract 30% (tested at 10 ppm) | 411 |
| Natural Spilanthol 95% (tested at 10 ppm) | 412 |
| Chilcuan Extract 25% (tested at 10 ppm) | 413 |
| Piper peepuloides (contains 5% mixture of $C_{10}$-$C_{11}$-E2,E4-alkadienamides of the invention) (tested at 10 ppm) | 414 |
| Piper longum Linn (contains 35% mixture of $C_{10}$-$C_{11}$-E2,E4-alkadienamides of the invention) (tested at 10 ppm) | 415 |
| Pelloritine 98% (tested at 10 ppm) | 416 |
| N-isobutyl-E2,Z6-dodecadienamide (tested at 10 ppm) | 417 |
| N-isobutyl-E2,E4,Z8-undecatrienamide (tested at 10 ppm) | 418 |

Figure 5:
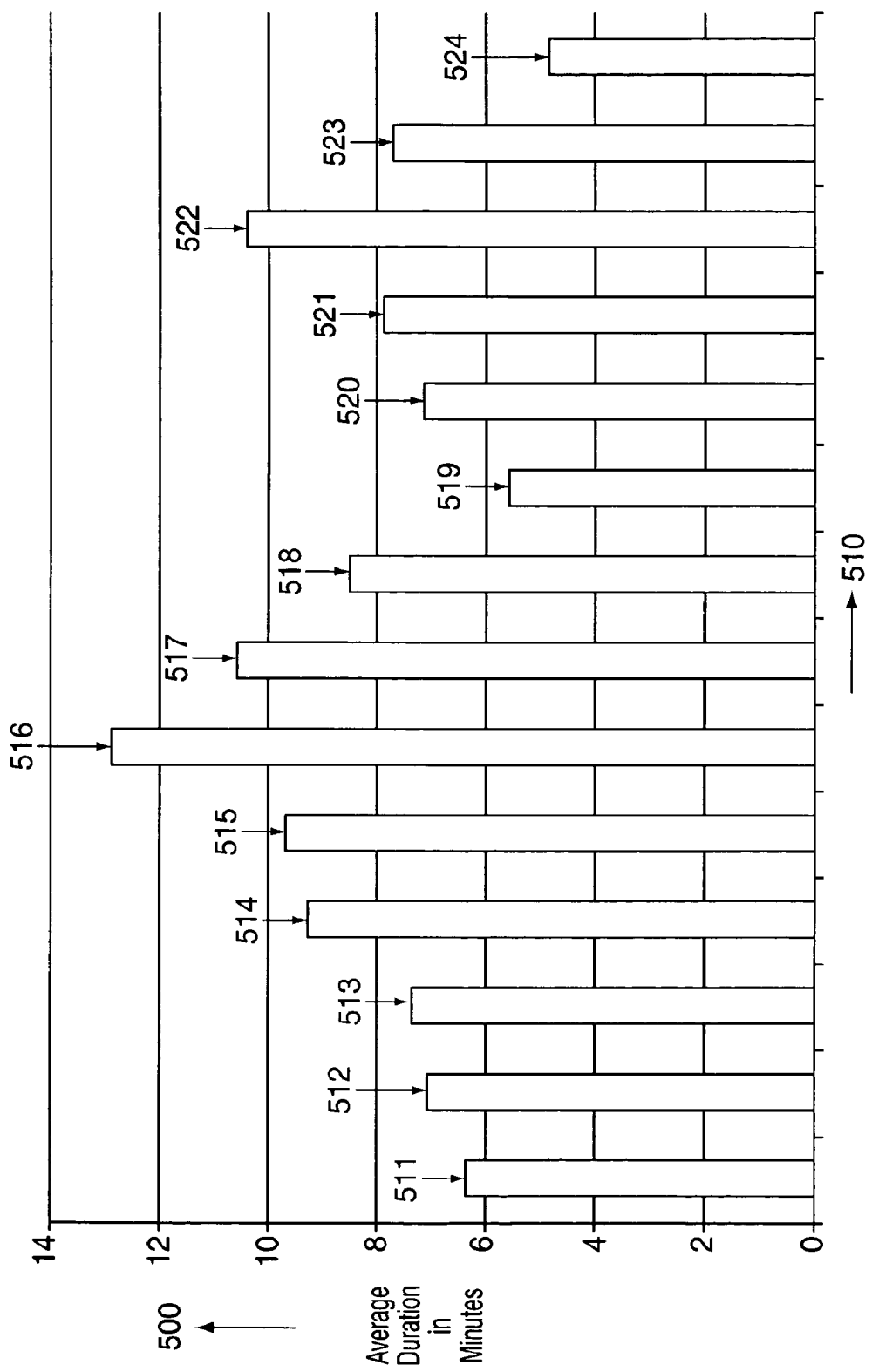
FIG. 5 is a set of bar graphs indicating duration in minutes for (i) extracts of *Piper longum* Linn and *Piper peepulides* containing various concentrations of $C_{10}$-$C_{11}$-E2,E4-alkadienamide mixtures of the invention, (ii) pellitorine, and (iii) other sensate substances.

Referring to FIG. 5, the "Y" axis indicated by reference numeral 500 indicates the time duration in minutes. The "X" axis, the horizontal axis, is indicated by reference numeral 510.

The following Table III sets forth the specific substance being compared identified by a specific reference numeral:

TABLE III

| Substance being compared | Reference Numeral |
| --- | --- |
| Jambu Extract 30% (tested at 10 ppm) | 511 |
| Chilcuan Extract 25% (tested at 10 ppm) | 512 |
| Chilcuan Extract 25% (tested at 20 ppm) | 513 |
| Piper longum Linn (contains 35% mixture of $C_{10}$-$C_{11}$-E2,E4-alkadienamides of the invention)(tested at 10 ppm) | 514 |
| Piper longum Linn (contains 25% mixture of $C_{10}$-$C_{11}$-E2,E4-alkadienamides of the invention)(tested at 10 ppm) | 515 |
| Piper longum Linn (contains 7% mixture of $C_{10}$-$C_{11}$-E2,E4-alkadienamides of the invention)(tested at 10 ppm) | 516 |

TABLE III-continued

| Substance being compared | Reference Numeral |
| --- | --- |
| Piper peepuloides (contains 5% mixture of $C_{10}$-$C_{11}$-E2,E4-alkadienamides of the invention) (tested at 10 ppm) | 517 |
| Pelloritine 98% (tested at 10 ppm) | 518 |
| Natural spilanthol 95% (tested at 20 ppm) | 519 |
| Natural spilanthol 95% (tested at 10 ppm) | 520 |
| N-isobutyl-E2,E4,Z8-undecatrienamide (tested at 20 ppm) | 521 |
| N-isobutyl-E2,E4,Z8-undecatrienamide (tested at 10 ppm) | 522 |
| N-isobutyl-E2,Z6-nonadienamide (tested at 10 ppm) | 523 |
| N-isobutyl-E2,Z6-undecadienamide (tested at 10 ppm) | 524 |

The following examples are provided as specific embodiments of the present invention. Other modifications of this invention will be readily apparent to those skilled in the art, without departing from the scope of this invention. As used herein, both the specification and the following examples all percentages are weight percent unless noted to the contrary.

EXAMPLE 1

Preparation of Components of Mixtures of $C_{10}$-$C_{11}$-E2,E4-Alkadienamides

The following reaction sequence was used to prepare the specific compounds described by the NMR data set forth below:

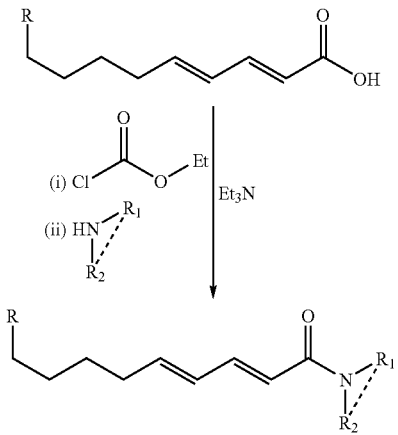

2,4-Dienoic acid was dissolved in dichloromethane to which ethylchloroformate was added in 1.0 to 2.0 equivalents at temperature ranging from 0° C. to room temperature, most preferably from 10° C. to 20° C. The resulting solution was cooled to −10° C. to +10° C., and triethylamine was added in 1.0 to 2.0 equivalents such that the temperature range is below 10° C. and the mixture aged for 1 hour at room temperature. The mixture was filtered, and the filtrate cooled to 0° C.

The amine was added in 1.0 to 4.0 equivalents and the reaction was aged for about 1-3 hours at room temperature. The reaction was quenched with 10% aqueous hydrochloric acid, washed with 10% sodium hydroxide followed by sodium chloride solution, and the solvent was removed.

The crude product was purified by distillation or recrystallization depending on the physical properties. The reaction occurred in 40-60% mole yields based on the acids.

The amides were synthesized according to the general scheme above with the following specific examples. Equivalents set out are mole equivalents based on starting acid, yields are purified chemical yields based on starting acid.

N-isobutyl E2,E4-decadienamide

E2,E4-decadienoic acid 1 eq, ethyl chloroformate 1.5 eq, triethylamine 1.5 eq, isobutylamine 3.0 eq, quench as per general procedure, yield=45%.

| | |
|---|---|
| 0.89 ppm | (t, 3H, J = 6.92 Hz) |
| 0.92 ppm | (d, 6H, J = 6.71 Hz) |
| 1.30 ppm | (m, 4H) |
| 1.42 ppm | (pentet, 2H, J = 7.19 Hz) |
| 1.80 ppm | (septet, 1H, J = 6.73 Hz) |
| 2.14 ppm | (q, 2H, J = 6.88 Hz) |
| 3.16 ppm | (t, 2H, J = 6.48 Hz) |
| 5.57 ppm | (br. s, 1H) |
| 5.76 ppm | (d, 1H, J = 15.04 Hz) |
| 6.04-6.17 ppm | (m, 2H) |
| 7.19 ppm | (d, 1H, J = 14.98 Hz, of d, J = 9.85 Hz) |

N-isobutyl E2,E4-undecadienamide

E2,E4-undecadienoic acid 1 eq, ethyl chloroformate 1.5 eq, triethylamine 1.5 eq, isobutylamine 3.0 eq, quench as per general procedure, yield=40%.

| | |
|---|---|
| 0.88 ppm | (t, 3H, J = 6.82 Hz) |
| 0.92 ppm | (d, 6H, J = 6.70 Hz) |
| 1.28 ppm | (m, 6H) |
| 1.41 ppm | (pentet, 2H, J = 6.88 Hz) |
| 1.80 ppm | (septet, 1H, J = 6.73 Hz) |
| 2.14 ppm | (q, 2H, J = 6.83 Hz) |
| 3.16 ppm | (t, 2H, J = 6.48 Hz) |
| 5.55 ppm | (br. s, 1H) |
| 5.76 ppm | (d, 1H, J = 15.03 Hz) |
| 6.02-6.17 ppm | (m, 2H) |
| 7.19 ppm | (d, 1H, J = 14.98 Hz, of d, J = 9.86 Hz) |

N-piperidyl E2,E4-decadienamide

E2,E4-decadienoic acid 1 eq, ethyl chloroformate 1.1 eq, triethylamine 1.2 eq, piperidine 1.25 eq, quench as per general procedure, yield=40%.

| | |
|---|---|
| 0.89 ppm | (t, 3H, J = 6.92 Hz) |
| 1.30 ppm | (m, 4H) |
| 1.42 ppm | (pentet, 2H, J = 7.19 Hz) |
| 1.56 ppm | (m, 4H) |
| 1.64 ppm | (m, 2H) |
| 2.14 ppm | (q, 2H, J = 7.04 Hz) |
| 3.49 ppm | (br. s, 2H) |
| 3.60 ppm | (br. s, 2H) |
| 6.06 ppm | (m, 1H) |
| 6.18 ppm | (2d, 1H, J = 10.82 Hz) |
| 6.27 ppm | (d, 1H, J = 14.79 Hz) |
| 7.23 ppm | (d, 1H, J = 14.74 Hz, of d, J = 10.73 Hz) |

N-pyrrolidyl E2,E4-decadienamide

E2,E4-decadienoic acid 1 eq, ethyl chloroformate 1.1 eq, triethylamine 1.2 eq, pyrrolidine 1.5 eq, quench as per general procedure, yield=58%.

| | |
|---|---|
| 0.89 ppm | (t, 3H, J = 6.90 Hz) |
| 1.30 ppm | (m, 4H) |
| 1.42 ppm | (pentet, 2H, J = 7.10 Hz) |
| 1.86 ppm | (pentet, 2H, J = 7.40 Hz) |
| 1.96 ppm | (pentet, 2H, J = 6.50 Hz) |
| 2.15 ppm | (q, 2H, J = 7.10 Hz) |
| 3.53 ppm | (2t, 4H, J = 6.96 Hz) |
| 6.06-6.18 ppm | (m, 2H) |
| 6.09 ppm | (d, 1H, J = 14.87 Hz) |
| 7.27 ppm | (d, 1H, J = 14.83 Hz, of d, J = 10.57 Hz) |

EXAMPLE IIA

Preparation of Fragrance for Use in Shampoo of Example IIB

The following fragrance was prepared for use with the shampoo of Example II:

| Ingredients | Parts by Weight |
|---|---|
| α-irone | 7.0 |
| myristicin | 4.0 |
| 2-methoxynaphthalene | 3.0 |
| benzaldehyde | 2.0 |
| β-phenylethyl alcohol | 12.0 |
| nerol | 7.0 |
| eugenol | 8.0 |
| isoeugenol | 2.0 |
| amyl salicylate | 4.0 |
| β-caryophyllene | 14.0 |
| cedryl acetate | 16.0 |
| cyclohexyl salicylate | 4.0 |
| γ-dodecalactone | 3.0 |
| geranyl anthranilate | 3.0 |

EXAMPLE IIB

Preparation of Fragrance-Containing Shampoo Base for Use in Conjunction with Examples IIC, Infra At the rate of 0.8%, the fragrance was prepared according to Example IIA and admixed with the following aqueous shampoo base:

| Components | Parts by Weight |
|---|---|
| ammonium lauryl sulfate (27% aqueous solution) | 56.0 |
| citric acid | 0.50 |
| sodium citrate | 0.50 |
| coconut monoethanolamide | 5.0 |
| ethylene glycol distearate | 3.0 |
| methyl paraben | 0.50 |
| propyl paraben | 0.50 |
| color solution | 0.20 |
| water | 33.8 |

EXAMPLE IIC

To the shampoo of Example IIB, zinc pyrithione was added at the rate of 1%, and the following mixture, the components of which were prepared according to Example I, were added at the rate of 0.3%:

| Ingredients | Parts by Weight |
| --- | --- |
| N-isobutyl-E2,E4-decadienamide | 45 |
| N-isobutyl-E2,E4-undecadienamide | 25 |
| N-pyrollidyl-E2,E4-decadienamide | 5 |
| N-piperidyl-E2,E4-decadienamide | 10 |

A substantial tingling effect was exerted during use and 5 minutes post use of the shampoo, having a value of 9 on a scale of 1-9.

EXAMPLE III

EXAMPLE IIIA

Punch Flavor

The following punch flavor was prepared:

| Ingredients | Parts by Weight (grams) |
| --- | --- |
| benzaldehyde | 500 |
| single fold orange oil | 415 |
| single fold grapefruit flavor | 33.4 |
| ethyl caproate | 16.6 |
| ethyl butyrate | 16.6 |
| ethyl isovalerate | 8.3 |
| ethyl propionate | 3.3 |
| alpha ionone | 0.1 |
| jasmin absolute | 0.1 |
| geraniol | 3.3 |
| isoamyl acetate | 3.3 |
| 4,8-dimethyl-3,7-nonadien-2-yl 2-methyl-2-pentenoate | 6.5 |

EXAMPLE IIIB (i) Powder Flavor

20 Grams of the flavor composition of Example IIIA was emulsified in a solution containing 300 grams of gum acacia and 700 grams of water. The emulsion was spray-dried with a Bowen Lab Model Drier utilizing 250 cubic feet per minute of air with an inlet temperature of 500° F. and an outlet temperature of 200° F. and a wheel speed of 50,000 r.p.m.

(ii) Paste Blend

A mixture of 300 grams of the liquid flavor of Example IIIA and 1 kg. of Cab-O-Sil M-5 (Cabot Corporation of Boston, Mass.) silica was prepared by dispersing the silica in the liquid flavor with vigorous stirring. The powder flavor prepared according to part (i) was then blended into the resulting viscous liquid with stirring at 25° C. for a period of about 30 minutes resulting in a sustained release flavor paste.

EXAMPLE IIIC

Into a Hobart mixer, 98.15 parts by weight of sorbitol was admixed with 0.05 parts by weight of FD&C yellow #6 lake (Warner Jenkinson).

To the resulting mixture, with stirring the following substances were added:

(a) 0.60 parts by weight of the paste blend of Example IIIB;
(b) 0.40 parts by weight of groundcitric acid; and
(c) 0.30 parts by weight of the following mixture, the components of which were prepared according to Example I:

| Ingredients | Parts by Weight (grams) |
| --- | --- |
| N-Isobutyl-E2,E4-undecadienamide | 45 |
| N-isobutyl-E2,E4-undecadienamide | 25 |
| N-pyrollidyl-E2,E4-decadienamide | 5 |
| N-piperidyl-E2,E4-decadienamide | 10 |

0.8 parts by weight of magnesium stearate was then added to the resulting mixture and the resulting mixture was tabletted, providing orange-punch-flavored tablets with a pleasant 'tingle' effect.

What is claimed is:

1. A process for producing a mixture of at least four alkadienamides, each of which is defined according to the structure:

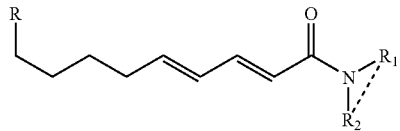

wherein R represents $C_1$-$C_2$ n-alkyl; $R_1$ is 2-methyl-1-propyl and $R_2$ is hydrogen, or $R_1$ and $R_2$ taken together is a moiety having the formula —$(CH_2)_n$—, wherein n is 5, the process comprising the steps of:

i. milling a dried fruit of *Piper longum* Linn to form a milled *Piper longum* Linn powder having an average particle size in the range of from about 300 to about 800 microns;

ii. providing an extractor equipped with a porous extractor plate;

iii. placing a portion of the milled *Piper longum* Linn powder on the porous extractor plate;

iv. contacting the thus-supported milled *Piper longum* Linn powder with a first quantity of a circulating polar solvent at a temperature in the range of from about 30 to about 50° C. for a period of time of from about 10 to about 20 hours with a first solvent to solid weight ratio being from about 2.75:1 to about 3.25:1, thereby forming a first extract and an initially-extracted milled *Piper longum* Linn powder;

v. removing the first extract from the extractor;

vi. contacting the initially-extracted milled *Piper longum* Linn powder with a second quantity of the circulating polar solvent at a temperature in the range of from about 30 to about 50° C. for a period of time of from about 10 to about 20 hours with a second solvent to solid weight ratio being from about 1.75:1 to about 2.25:1, thereby forming a second extract and a doubly-extracted milled *Piper longum* Linn powder;

vii. removing the second extract from the extractor;

viii. contacting the doubly-extracted milled *Piper longum* Linn powder with a third quantity of the circulating polar solvent at a temperature in the range of from about 30 to about 50° C. for a period of time of from about 10 to about 20 hours with a third solvent to solid weight ratio being from about 0.75:1 to about 1.25:1, thereby forming a third extract and a triply-extracted milled *Piper longum* Linn powder;

ix. removing the third extract from the extractor;

x(a). combining the first extract, the second extract, and the third extract to form a combined extract; and xi(a). subjecting the combined extract from step x(a) to a unit operation of evaporation to form a concentrated extract of the mixture.

2. The process of claim 1, wherein the extractor is a percolator and the porous plate is a screen basket.

3. The process of claim 1, wherein the solvent is n-hexane.

4. The process of claim 1 further comprising the step of fractionally distilling the concentrated extract of the mixture from step xi(a). at a vapor temperature in the range of from about 55 to about 76° C., a liquid temperature in the range of from about 109 to about 203° C., and a pressure in the range of from about 30 to about 60 mm Hg to form a distillate.

5. The process of claim 4 further comprising the step of admixing the distillate with a food-grade diluent.

6. The process of claim 4 further comprising the step of recovering the alkadienamides from the distillate.

7. A process for producing a mixture of at least four alkadienamides, each of which is defined according to the structure:

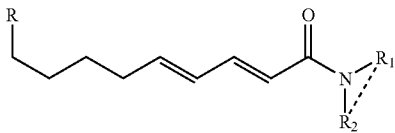

wherein R represents $C_1$ -$C_2$ n-alkyl; $R_1$ is 2-methyl-1-propyl and $R_2$ is hydrogen, or $R_1$ and $R_2$ taken together is a moiety having the formula —$(CH_2)_n$—, wherein n is 5, the process comprising the steps of:

i. milling a dried fruit of *Piper longum* Linn to form a milled *Piper longum* Linn powder having an average particle size in the range of from about 300 to about 800 microns;

ii. providing an extractor equipped with a porous extractor plate;

iii. placing a portion of the milled *Piper longum* Linn powder on the porous extractor plate;

iv. contacting the thus-supported milled *Piper longum* Linn powder with a first quantity of a circulating polar solvent at a temperature in the range of from about 30 to about 50° C. for a period of time of from about 10 to about 20 hours with a first solvent to solid weight ratio being from about 2.75:1 to about 3.25:1, thereby forming a first extract and an initially-extracted milled *Piper longum* Linn powder;

v. removing the first extract from the extractor;

vi. contacting the initially-extracted milled *Piper longum* Linn powder with a second quantity of the circulating polar solvent at a temperature in the range of from about 30 to about 50° C. for a period of time of from about 10 to about 20 hours with a second solvent to solid weight ratio being from about 1.75:1 to about 2.25:1, thereby forming a second extract and a doubly-extracted milled *Piper longum* Linn powder;

vii. removing the second extract from the extractor;

viii. contacting the doubly-extracted milled *Piper longum* Linn powder with a third quantity of the circulating polar solvent at a temperature in the range of from about 30 to about 50° C. for a period of time of from about 10 to about 20 hours with a third solvent to solid weight ratio being from about 0.75:1 to about 1.25:1, thereby forming a third extract and a triply-extracted milled *Piper longum* Linn powder;

ix. removing the third extract from the extractor;

x(b). contacting the triply-extracted milled *Piper longum* Linn powder with a fourth quantity of the circulating polar solvent, thereby forming a fourth extract and a quadruply-extracted milled *Piper longum* Linn powder; and xi(b). removing the fourth extract from the extractor;

xii(b). combining the first extract, the second extract, the third extract, and the fourth extract to form a combined extract; and xiii(b). subjecting the combined extract from step xii(b) to a unit operation of evaporation to form a concentrated extract of the mixture.

8. The process of claim 7, wherein the solvent is 95% aqueous ethanol.

9. The process of claim 7 further comprising the step of fractionally distilling the concentrated extract of the mixture from step xiii(b). at a vapor temperature in the range of from about 55 to about 76° C., a liquid temperature in the range of from about 109 to about 203° C., and a pressure in the range of from about 30 to about 60 mm Hg to form a distillate.

10. The process of claim 9 further comprising the step of admixing the distillate with a food-grade diluent.

11. The process of claim 9 further comprising the step of recovering the alkadienamides from the distillate.

12. The process of claim 7, wherein the solvent is n-hexane.

* * * * *